(12) United States Patent
Ahrens

(10) Patent No.: US 12,042,588 B2
(45) Date of Patent: *Jul. 23, 2024

(54) OXYGENATOR UNIT WITH A PRESSURE RELIEF VALVE

(71) Applicant: B. Braun Avitum AG, Melsungen (DE)

(72) Inventor: Jörn Ahrens, Baunatal (DE)

(73) Assignee: B. Braun Avitum AG, Melsungen (DE)

( * ) Notice: Subject to any disclaimer, the term of this patent is extended or adjusted under 35 U.S.C. 154(b) by 687 days.

This patent is subject to a terminal disclaimer.

(21) Appl. No.: 17/239,869

(22) Filed: Apr. 26, 2021

(65) Prior Publication Data

US 2021/0236706 A1 Aug. 5, 2021

Related U.S. Application Data

(63) Continuation of application No. 16/029,941, filed on Jul. 9, 2018, now Pat. No. 11,013,842.

(30) Foreign Application Priority Data

Jul. 10, 2017 (EP) ...................................... 17180539

(51) Int. Cl.
*A61M 1/16* (2006.01)

(52) U.S. Cl.
CPC ....... *A61M 1/1698* (2013.01); *A61M 2205/18* (2013.01); *A61M 2205/3303* (2013.01);
(Continued)

(58) Field of Classification Search
CPC ............ A61M 1/1698; A61M 2205/18; A61M 2205/3303; A61M 2205/3331; A61M 2205/3334; A61M 2205/3341
See application file for complete search history.

(56) References Cited

U.S. PATENT DOCUMENTS

| 3,877,843 A | 4/1975 | Fischel |
| 3,927,980 A | 12/1975 | Leonard |

(Continued)

FOREIGN PATENT DOCUMENTS

| EP | 0283850 A2 | 9/1988 |
| GB | 2561221 A | 10/2018 |

(Continued)

OTHER PUBLICATIONS

Tonglinger, et al., "Basic Principles of Mechanical Manufacturing Engineering," 2nd Edition, Hunan Science and Technology Press, dated Jan. 31, 2013, with translation, 21 pages.

(Continued)

*Primary Examiner* — Jessica Arble
(74) *Attorney, Agent, or Firm* — Christopher A Rothe; Culhane PLLC

(57) ABSTRACT

An oxygenator unit adapted for the use in an extracorporeal blood treatment device. The oxygenator unit includes an oxygenator having a gas inlet and a supply line for conducting a gas provided at the gas inlet, the supply line being connectable to a source of a pressurized gas containing oxygen, wherein the oxygenator unit further includes a pressure relief valve provided in the supply line upstream of the oxygenator, the pressure relief valve being adapted to release pressure exceeding a predetermined pressure value from the supply line, thereby preventing a critical overpressure in the oxygenator.

9 Claims, 3 Drawing Sheets

(52) U.S. Cl.
CPC ............... *A61M 2205/3331* (2013.01); *A61M 2205/3334* (2013.01); *A61M 2205/3341* (2013.01)

(56) References Cited

U.S. PATENT DOCUMENTS

| | | |
|---|---|---|
| 4,715,959 A | 12/1987 | Allan et al. |
| 5,120,502 A | 6/1992 | Gordon et al. |
| 5,158,534 A | 10/1992 | Berry et al. |
| 10,335,531 B2 | 7/2019 | Gipson |
| 11,013,842 B2 * | 5/2021 | Ahrens ............... A61M 1/1698 |
| 2002/0114705 A1 | 8/2002 | Schnatterer |
| 2002/0138034 A1 | 9/2002 | Derek et al. |
| 2003/0091470 A1 | 5/2003 | Patterson et al. |
| 2006/0162725 A1 * | 7/2006 | Downie ............... A61M 16/22 128/203.12 |
| 2006/0231098 A1 | 10/2006 | Downie et al. |
| 2007/0009881 A1 | 1/2007 | Arzt et al. |
| 2007/0246999 A1 | 10/2007 | Hilberer |
| 2009/0081079 A1 | 3/2009 | Johns |
| 2009/0230058 A1 | 9/2009 | Boris-Moeller |
| 2012/0035523 A1 | 2/2012 | Farnikova |
| 2016/0220746 A1 | 8/2016 | Gipson |
| 2018/0344918 A1 | 12/2018 | Turner et al. |
| 2019/0344005 A1 | 11/2019 | Larsson |

FOREIGN PATENT DOCUMENTS

| | | |
|---|---|---|
| JP | 6303870 A | 1/1988 |
| JP | H04197265 A | 7/1992 |
| JP | H06503725 A | 4/1994 |
| JP | 2016536034 A | 11/2016 |
| WO | 9200777 A1 | 1/1992 |
| WO | 2009029801 A2 | 3/2009 |
| WO | 2015047927 A1 | 4/2015 |

OTHER PUBLICATIONS

Office Action received in Chinese Application No. 201810745275.6 dated Jan. 28, 2023, with translation, 20 pages.
Office Action received in Japanese Application No. 2018-130488 dated Jun. 7, 2022, with translation, 7 pages.
Office Action received in Chinese Application No. 201810745275.6 dated Jun. 14, 2023, with translation, 12 pages.
Communication under Rule 71(3) EPC received in Application No. 17 180 539.3-1113 dated Dec. 5, 2022, 24 pages.
Office Action received in Chinese Application No. 201810745275.6 dated May 6, 2022, with translation, 19 pages.
Extended European Search Report received in Application No. 17180539.3 dated Dec. 21, 2017, 7 pages.

* cited by examiner

OXYGENATOR UNIT WITH A PRESSURE RELIEF VALVE

CROSS REFERENCE TO RELATED APPLICATIONS

This application is a continuation of U.S. application Ser. No. 16/029,941 filed Jul. 9, 2018, which claims priority to European application EP 17 180 539.3 filed Jul. 10, 2017, the contents of such application being incorporated by reference herein.

FIELD OF THE INVENTION

The present invention relates to an oxygenator unit for an extracorporeal blood treatment device and an extracorporeal blood treatment device comprising a blood treatment unit, preferably a dialyzer, and an oxygenator that is used to enrich the treated blood with oxygen and remove carbon dioxide from the treated blood.

BACKGROUND OF THE INVENTION

Extracorporeal blood treatment units comprising an oxygenator are applied in the field of haemodialysis treatment of acute patients who are also in need of carbon dioxide removal from the blood.

DESCRIPTION OF THE RELATED ART

Oxygenator units and extracorporeal blood treatment devices of the above mentioned types are commonly known from the prior art. As examples, oxygenators used in an extracorporeal blood treatment device are known from WO 2009/029801, U.S. Pat. No. 3,877,843 and EP 0 283 850.

It is a drawback of the oxygenators and/or extracorporeal blood treatment devices of the prior art that under certain circumstances during operation, air bubbles on the blood side of the oxygenator may occur, leading to a variety of complications depending on the position of the oxygenator. For example, if the oxygenator is positioned upstream of the dialyzer, air bubbles occurred in the oxygenator may stay in the dialyzer and may cause severe impact on the performance of the dialyzer and increase clotting due to increased air-blood-contact.

Moreover, the presence of air bubbles in the extracorporeal treated blood poses a dangerous risk to the patient's health and life, which is why the supply of a device for removing air bubbles is required in the extracorporeal blood treatment device.

For this purpose, in the prior art there are removing devices for air bubbles, e.g. bubble traps, positioned in the arterial and the venous tube system to prevent air bubbles from flowing into the patient's body. However, as a further drawback of the prior art, the effectiveness and reliability of commonly used bubbles traps have been proved limited in their performance, since common bubble traps fail to remove air bubbles below a certain size. Therefore, the so-called micro bubbles remain on the blood side and cannot be removed reliably by the bubble trap.

SUMMARY OF THE INVENTION

Compared to this, it is an object of the invention to provide an oxygenator unit and/or an extracorporeal blood treatment device, in which the extracorporeal guided blood is substantially free of any air bubbles.

This object is achieved by an oxygenator unit comprising the features of the independent claim and/or an extracorporeal blood treatment device comprising the features of a blood treatment unit and the oxygenator unit of the independent claim.

Advantageous further developments of the oxygenator unit and advantageous further developments of the extracorporeal blood treatment device are described in the dependent claims.

The underlying general idea of the invention is to reliably and safely prevent the generation of air bubbles on the blood side of the oxygenator in the first place. Therefore, the exchange of substances, such as oxygen or carbon dioxide, between the gaseous side and the blood side in the oxygenator is conducted below or at the thermodynamic equilibrium. That is to say that the transfer of a gaseous substance from the gaseous side to the blood side of the oxygenator, thereby passing the membrane of the oxygenator, is carried out exclusively by diffusion to ensure that the substances which pass the membrane from the gaseous side to the blood side will be fully dissolved in the flowing blood. In other words, the concentration of a (former gaseous) substance on the blood side is held below or on the limit of solubility.

The thermodynamic equilibrium can be controlled by the parameters of both sides of the oxygenator, e.g. by pressure and temperature of the gaseous side and the blood side. Since the temperature and pressure on the blood side should correspond to the physiological condition of the human body (atmospheric pressure), the equilibrium in the oxygenator is controlled by the parameters on the gaseous side and according to aspects of the invention by pressure control.

Additionally, the operating condition in the oxygenator shall be protected against misadjustment of the user or technical defects of the resource to be connected. For example, in the standard clinic installation air flow regulators for adjusting the gaseous flow are provided. If the air flow regulator is technically unreliable or the operator of the air flow regulator makes a mistake in the settings, the demanded operating conditions in the oxygenator will not be met, posing the patient at risk.

According to aspects of the invention, an object is achieved by an oxygenator unit adapted for the use/incorporation/mounting in an extracorporeal blood treatment device, the oxygenator unit comprising an oxygenator and a supply line, e.g. a flexible tube, for conducting a gas, the supply line being provided at a gas inlet of the oxygenator and connectable to a source of a pressurized gas containing oxygen, e.g. medical air supplied by the clinic via a wall installation, wherein the oxygenator unit further comprises a pressure relief valve, e.g. a mechanical or electrically adapted valve, which is provided in the supply line upstream of the gas inlet of the oxygenator, the pressure relief valve being adapted to release pressure exceeding a predetermined pressure value from the supply line, thereby preventing a critical overpressure in the oxygenator. Alternatively, the pressure relief valve may be integrated in a connector of a gas inlet port of the oxygenator.

It as a beneficial effect of the pressure relief valve that its opening pressure is structurally set and thus not adjustable or alterable, preventing misadjustments of the operator. The pressure relief valve is chosen dependent on the oxygenator to be used and matched to the character of the membrane separating the gaseous side from the blood side, thereby making sure that the pressure limit at which the valve opens is below the pressure at which air bubbles can develop on the blood side. The entire oxygenator unit shall preferably be manufactured as one disposable unit, for hygienic reasons as well as to assure an appropriate combination of valve and oxygenator.

The supply line can be connected to any kind of common wall installations in the clinic infrastructure, e.g. the supply line can be connected to the gas source via an air flow regulator provided at the wall installation. In case the air flow regulator is incorrectly set or defective, the pressure relief valve according to aspects of the invention serves as an additional safety measure to control pressure in the oxygenator.

Preferably, the pressure value at which the pressure relief valve releases pressure from the supply line is between a pressure value of 66 hPa (50 mmHg) and 134 hPa (100 mmHg), particularly between 93 hPa (60 mmHg) and 120 hPa (80 mmHg) and more particularly 100 hPa (75 mmHg). It has been found that pressure values in this range do not exceed the resistance of the membrane of the oxygenator, ensuring that the exchange of substances between gas and blood are exclusively carried out by diffusion.

Especially preferred, a pressure sensor is provided between an inlet of the pressure relief valve and the gas inlet of the oxygenator, in particular between an outlet of the pressure relief valve and the gas inlet of the oxygenator such that the pressure on the supply line downstream of the valve, that is to say in the oxygenator, can be measured and/or monitored with an external system to provide additional safety to the therapy process.

Additionally preferred, an air flow sensor is provided between an outlet of the pressure relief valve and the gas inlet of the oxygenator such that in the air flow in the supply line downstream of the valve, thus in the oxygenator, can be measured and/or monitored with an external system to provide additional safety to the therapy process.

Further preferred, the oxygenator unit comprises a measuring means for measuring gas parameters, e.g. concentration of substances as oxygen and/or carbon dioxide, at the gas inlet of the oxygenator and at the gas outlet of the oxygenator. This allows additional monitoring with an external system of the therapy process and safety for the patient. Especially since the purpose of the oxygenator is to exchange carbon dioxide from the blood for oxygen, the progress of this therapy step can be determined.

In order to keep the technical effort low, an oxygenator type with a single outlet port is preferred. There are oxygenator types available which are equipped with a further air outlet port (usually of smaller size than the regular outlet and open to the environment) additional to the regular air outlet of the oxygenator in order to avoid a blockage of the gas flow in case the outflow line provided at the gas outlet of the oxygenator is kinked. However, to allow unimpaired and accurate measurement of the parameters of the outflowing gas, a measuring means for gas parameters should be provided at every gas outlet of the oxygenator.

The one or more sensors and/or measuring means can be used to provide feedback to an external system that gives an alarm in case of failure.

Moreover, an object of the invention is achieved by an extracorporeal blood treatment device comprising a blood treatment unit, e.g. a dialyzer such as a haemofilter, and an oxygenator unit as described above.

Preferably, the extracorporeal blood treatment device further comprises a control unit which is connected to at least one sensor and/or measuring means of the oxygenator and to an alarm, the control unit initiating an alarm signal in case a measured signal crosses a predetermined threshold.

It is an advantage to provide the extracorporeal blood treatment device with an alarm system, since the operator can be alerted in case the measured parameters, e.g. sensed by one of the sensors or measuring means described above, deviate from a determined range.

BRIEF DESCRIPTION OF THE DRAWINGS aspects of The invention is best understood from the following detailed description when read in connection with the accompanying drawings. Included in the drawings are the following figures.

DETAILED DESCRIPTION OF THE PREFERRED EMBODIMENTS

Figure 1:
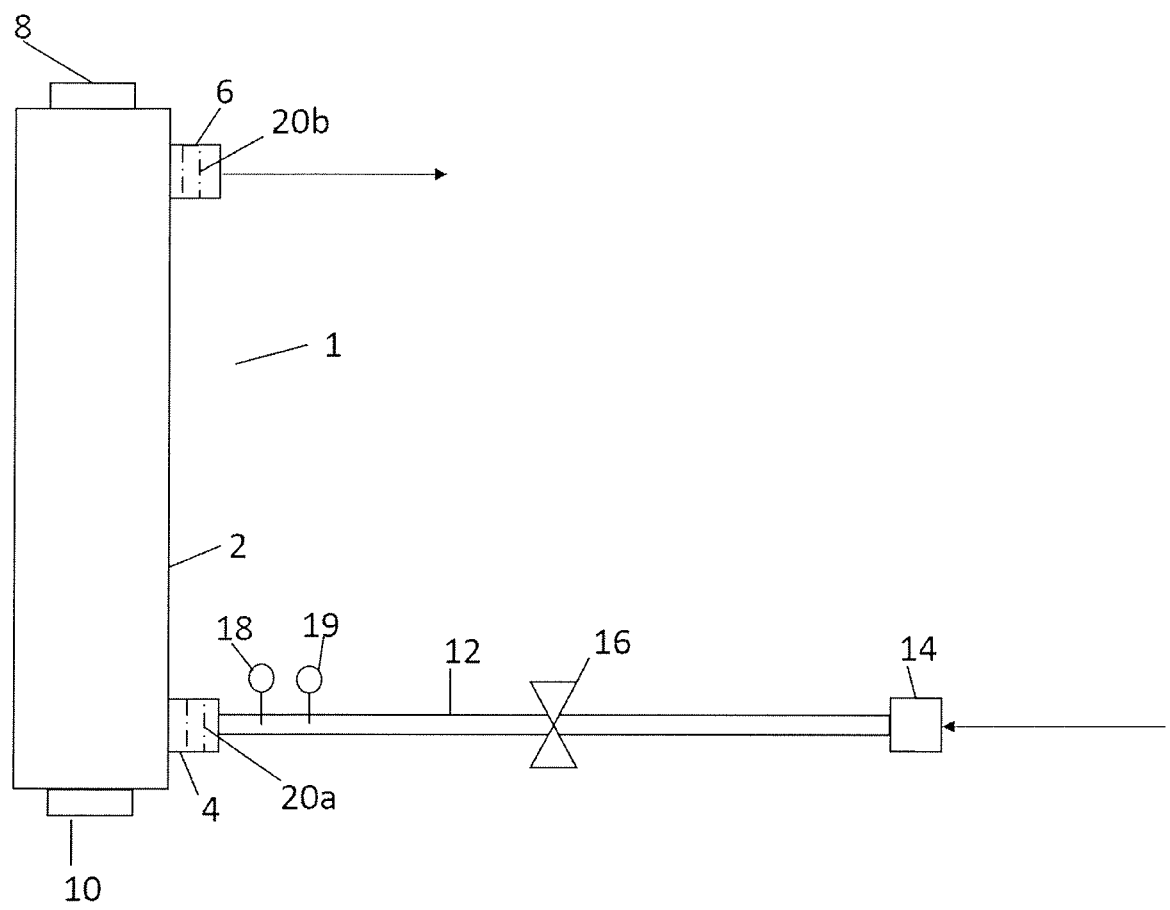
FIG. 1 shows a schematic representation of an oxygenator unit according to aspects of the invention.

FIG. 1 shows an oxygenator unit 1 in an embodiment according to aspects of the invention. The oxygenator 2 has a gas inlet port 4, a gas outlet port 6, a blood inlet port 8 and a blood outlet port 10. The arrows indicate the flow direction of gas. A supply line 12 is provided at the gas inlet 4. The supply line 12 can be fixed to the gas inlet 4 by any commonly known connection means and/or methods, e.g. the supply line 12 can be plugged on the gas inlet 4, fixed by clamps, adhesive or the like. The end of the supply line 12 opposite to the gas inlet 4 has a connection means 14 by which the supply line 12 can be coupled to a gas source. The connection means 14 can be of any commonly known type, e.g. a plug connection, screw connection, potentially in combination with fastening elements. Between the connection means 14 and the gas inlet 4, a pressure relief valve 16 is positioned. The pressure relief valve 16 is constructed such that the valve opens above a predetermined pressure value of inflowing gas, wherein the pressure relief valve 16 is selected in coordination with the required pressure limit according to aspects of the provided oxygenator 2, e.g. the pressure relief valve 16 opens above a pressure of 100 hPa. In the supply line 12 a sensor 18 for measuring pressure and a sensor 18 for measuring air flow are provided. In or in the area of the gas inlet port 4 and/or in or in the area of the gas outlet port 6 a measuring means 20a and 20b is positioned to measure one or more parameters of the gas passing the measuring means, e.g. concentration of oxygen and/or carbon dioxide. It is possible to arrange additional sensors/measuring means in the oxygenator 1 and/or supply 12 such as temperature or humidity sensors and the like.

Figure 2:
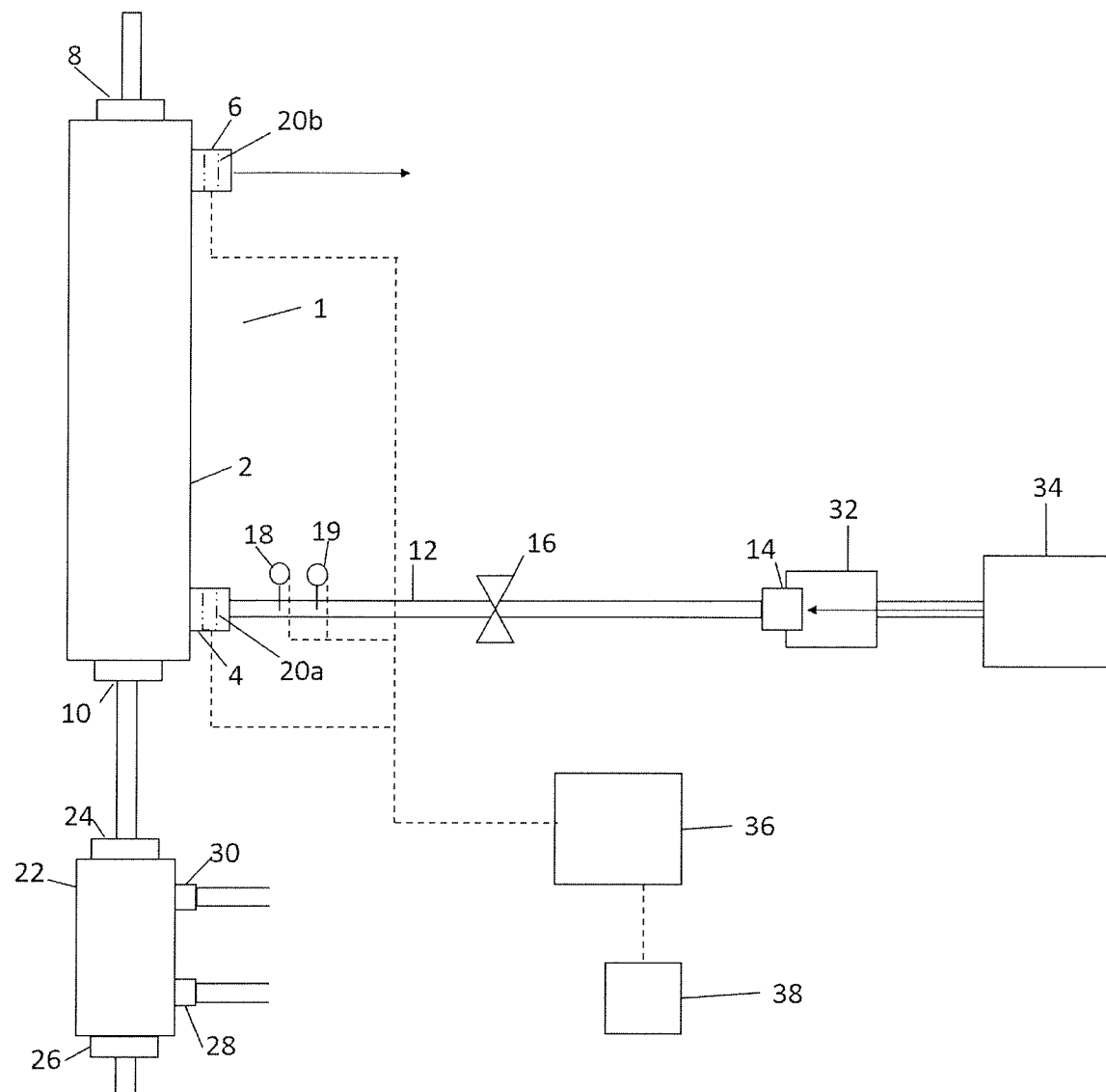
FIG. 2 shows a schematic representation of an extracorporeal blood treatment device according to aspects of the invention.

FIG. 2 shows an extracorporeal blood treatment device according to aspects of an embodiment of the invention. The extracorporeal blood treatment device comprises an oxygenator unit 1 as described above and a dialyzer 22, e.g. a haemofilter or haemodiafilter, with a blood inlet port 24, a blood outlet port 26, an inlet port for dialysis fluid 28 and an outlet port for dialysis fluid 30. The connection means 14 of the supply line 12 is coupled to an air flow regulator 32 which is part of a standard clinic wall installation. The air flow regulator 32 is provided downstream of a gas source 34, which is part of the standard clinic infrastructure.

Figure 3:
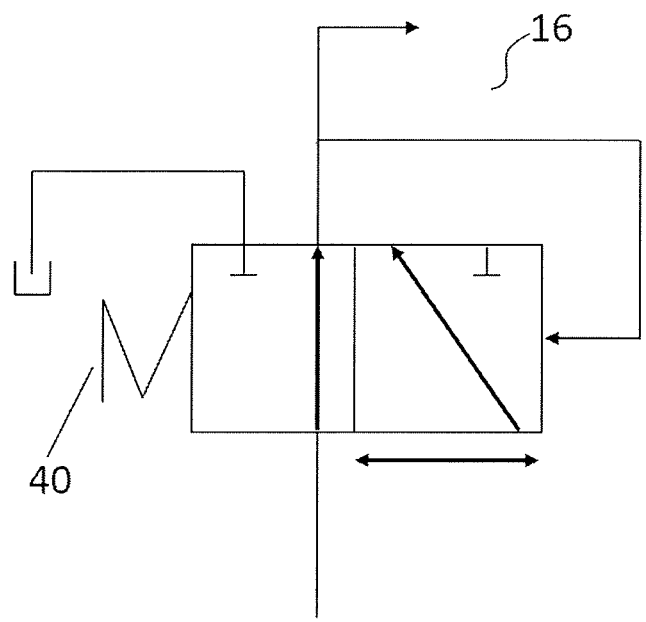
FIG. 3 shows a schematic representation of a mechanical pressure relief valve according to aspects of the invention.

FIG. 3 shows a mechanical pressure relief valve 16 as a 3/2 switching valve provided with a spring 40. When the line in which the valve is positioned is exposed to pressure and the pressure is below a predetermined pressure threshold, the spring 40 holds the valve is in the open position, that is to say the line is open. When the pressure exceeds a predetermined pressure threshold, the force of the spring 40 is exceeded and the valve is switched to the closed position, that is to say the line is closed (and the pressure is released through another opening of the valve).

Figure 4:
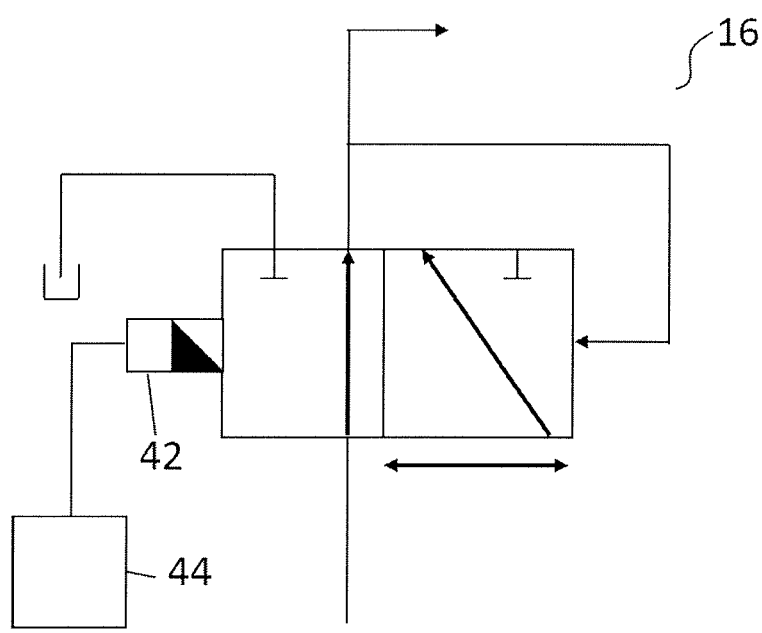
FIG. 4 shows a schematic representation of an electrically adapted pressure relief valve according to aspects of the invention.

FIG. 4 shows an electrically adapted pressure relief valve 16 as a 3/2 switching valve provided with a piezo element 42 and a corresponding control unit 44. The electrically adapted valve operates analogously to the afore described mechanical valve, with the difference that instead of a spring 40, a piezo element 42 is provided with a control unit 44, by which the piezo element 42 can be set.

In operation, when the oxygenator unit 1 is connected to the gas source 34 via a coupling of the connection means 14 of the supply line 12 with the air flow regulator 32, medical gas containing oxygen is flowing from the gas source through the air flow regulator 32 in the direction of the gas inlet port 4, thereby passing the pressure relief valve 16. In case the pressure of gas flowing from the gas source 34 to the pressure relief valve 16 exceeds a predetermined pressure value, the pressure relief valve 16 opens so that in the portion of the supply line 12 which extends from the outlet of the pressure relief valve 16 to the gas inlet port 4 the pressure of gas is below or equals the predetermined pressure value. The pressure relief valve 14 functions independently of the air flow regulator 32 and thus functions as an additional safety means. The sensors 18 and 19 and/or the measuring means 20a and 20b are connected to a control unit 36 and provide feedback signals to the control unit 36. In case of failure an alarm 38 can be triggered by the control unit 36.

A flexible tube connects the blood outlet port 10 of the oxygenator 2 with the blood inlet port 24 of the dialyzer 22. At the blood outlet port 26 of the dialyzer 22 another tube is attached to guide the blood back to the patient. During therapy, extracorporeal guided blood flows through the oxygenator 2 entering the oxygenator 2 at the blood inlet port 8 of the oxygenator 2 and exits the oxygenator 2 at the blood outlet port 10 of the oxygenator 2. While passing the oxygenator 2, carbon dioxide is transferred (exclusively by diffusion) from the blood running through the blood side of the oxygenator 2 via the membrane to the gas flowing through the gas side of the oxygenator 2 and oxygen is transferred (exclusively by diffusion) in the opposite direction from the gas via the membrane to the blood. As a result, the blood leaves the oxygenator 2 enriched with oxygen and lowered in carbon dioxide. Due to the pressure relief valve 16 it is ensured that the blood is essentially free from air bubbles.

After being oxygenated, the blood enters the dialyzer 22 through the blood inlet port 24, flows through the dialyzer 22 and leaves the dialyzer 22 through the blood outlet port 26. Inside the dialyzer 22, the blood is treated with dialysis fluid, which enters the dialyzer 22 through the inlet port for dialysis fluid 28 and leaves the dialyzer 22 through the outlet port for dialysis fluid 30.

It is also possible to have the oxygenator 2 positioned downstream of the dialyzer 22.

Summing up, aspects of the invention relate to an oxygenator unit with an overpressure valve added to the inlet air/gas line of the oxygenator between an air flow regulator and the oxygenator gas inlet port, wherein the overpressure valve opens in case the pressure against atmosphere is higher than a predetermined threshold, preferably higher than 50 mmHg to 100 mmHg.

The invention claimed is:

1. An extracorporeal blood treatment device, comprising:
   A) an oxygenator unit comprising:
      i) an oxygenator having a gas inlet port;
      ii) a supply line for conducting a gas, the supply line provided at the gas inlet port of the oxygenator and connectable to a source of a pressurized gas containing oxygen; and
      iii) a pressure relief valve provided in the supply line upstream of the oxygenator, the pressure relief valve having an open position and a closed position and configured to release pressure exceeding a predetermined pressure threshold value from the supply line to prevent a critical overpressure in the oxygenator, the pressure relief valve including a spring or a piezo element;
   B) a blood treatment unit configured to treat blood passing through the blood treatment unit; and
   C) a flexible blood tube fluidly connected between the oxygenator and the blood treatment unit for supplying blood to the blood treatment unit,
   wherein, when the supply line is exposed to pressure below the predetermined pressure threshold value, the spring or the piezo element holds the pressure relief valve in the open position and, when the pressure exceeds the predetermined pressure threshold, the pressure relief valve is switched to the closed position.

2. The oxygenator unit according to claim 1, wherein the predetermined pressure threshold value at which the pressure relief valve releases pressure from the supply line is between a pressure value of 66 hPa and 134 hPa.

3. The oxygenator unit according to claim 1, further comprising:
   a pressure sensor provided between an inlet of the pressure relief valve and the gas inlet port of the oxygenator.

4. The oxygenator unit according to claim 1, further comprising:
   an air flow sensor provided between an outlet of the pressure relief valve and the gas inlet port of the oxygenator.

5. The oxygenator unit according to claim 1, further comprising:
   a measuring means for measuring gas parameters at the gas inlet port of the oxygenator and at a gas outlet port of the oxygenator.

6. The extracorporeal blood treatment device according to claim 1, further comprising:
   a control unit connected to at least one sensor or at least one measuring means, or at least one sensor and at least one measuring means, of the oxygenator and to an alarm, the control unit configured to initiate an alarm signal when a measured signal from the at least one sensor or the at least one measuring means, or at least one sensor and at least one measuring means, of the oxygenator crosses a predetermined threshold.

7. The extracorporeal blood treatment device according to claim 1, wherein the oxygenator further comprises a gas outlet port, a blood inlet port, and a blood outlet port.

8. The extracorporeal blood treatment device according to claim 7, wherein the flexible blood tube is connected to the blood outlet port of the oxygenator.

9. The extracorporeal blood treatment device according to claim 1, wherein the blood treatment unit is a dialyzer unit.

\* \* \* \* \*